United States Patent
Schulman et al.

(10) Patent No.: US 6,185,452 B1
(45) Date of Patent: Feb. 6, 2001

(54) BATTERY-POWERED PATIENT IMPLANTABLE DEVICE

(76) Inventors: Joseph H. Schulman, 16050 Comet Way, Santa Clarita; Robert Dan Dell, 19315 Old Friend Rd., Canyon Country, both of CA (US) 91351; John C. Gord, 806 Indiana Ave., Venice, CA (US) 90291

( * ) Notice: Under 35 U.S.C. 154(b), the term of this patent shall be extended for 0 days.

(21) Appl. No.: 09/030,106

(22) Filed: Feb. 25, 1998

Related U.S. Application Data

(60) Provisional application No. 60/039,164, filed on Feb. 26, 1997.

(51) Int. Cl.[7] ............................... A61N 1/30; A61N 1/08
(52) U.S. Cl. .................................................. 604/20; 607/60
(58) Field of Search ........................... 604/20, 21, 890.1, 604/891.1, 93; 128/899; 607/2, 9, 17, 30, 32, 33, 39–48, 50–57, 60–65

(56) References Cited

U.S. PATENT DOCUMENTS

| | | | | |
|---|---|---|---|---|
| 4,146,029 | * | 3/1979 | Ellinwood, Jr. ....................... 128/260 |
| 4,360,019 | * | 11/1982 | Portner et al. ..................... 604/891.1 |
| 4,619,653 | * | 10/1986 | Fischell ............................. 604/891.1 |
| 4,714,462 | * | 12/1987 | DiDomenico .......................... 604/67 |
| 5,167,625 | * | 12/1992 | Jacobsen et al. .................. 604/891.1 |
| 5,170,801 | * | 12/1992 | Casper et al. .......................... 128/769 |
| 5,193,539 | * | 3/1993 | Schulman et al. ............... 128/419 R |
| 5,193,540 | * | 3/1993 | Schulman et al. ............... 128/419 R |
| 5,279,607 | * | 1/1994 | Schentag et al. ................. 604/890.1 |
| 5,312,439 | * | 5/1994 | Loeb ....................................... 607/2 |
| 5,324,316 | | 6/1994 | Schulman et al. ..................... 607/61 |
| 5,358,514 | * | 10/1994 | Schulman et al. ..................... 607/61 |
| 5,405,367 | | 4/1995 | Schulman et al. ..................... 607/61 |
| 5,507,737 | * | 4/1996 | Palmskog ............................... 604/93 |
| 5,544,651 | * | 8/1996 | Wilk .................................. 604/890.1 |
| 5,558,640 | * | 9/1996 | Pfeiler et al. .......................... 604/67 |
| 5,571,148 | * | 11/1996 | Loeb et al. ............................. 607/57 |
| 5,591,217 | | 1/1997 | Barreras ................................. 607/61 |
| 5,782,799 | * | 7/1998 | Jacobsen et al. ....................... 604/49 |

* cited by examiner

Primary Examiner—Sharon Kennedy
(74) Attorney, Agent, or Firm—Freilich, Hornbaker & Rosen

(57) ABSTRACT

A device configured for implanting beneath a patient's skin for the purpose of tissue, e.g., nerve or muscle, stimulation and/or parameter monitoring and/or data communication. Devices in accordance with the invention are comprised of a sealed housing, typically having an axial dimension of less than 60 mm and a lateral dimension of less than 6 mm, containing a power source for powering electronic circuitry within including a controller, an address storage means, a data signal receiver and an input/output transducer. When used as a stimulator, such a device is useful in a wide variety of applications to stimulate nerves and associated neural pathways, e.g., to decrease or relieve pain, stimulate specific muscles or organs to better carry out a body function (e.g., to exercise weak or unconditioned muscles or to control urinary incontinence), and the like. Alternatively, devices of the present invention are configurable to monitor a biological parameter or to operate as a transponder to retransmit received command messages.

20 Claims, 13 Drawing Sheets

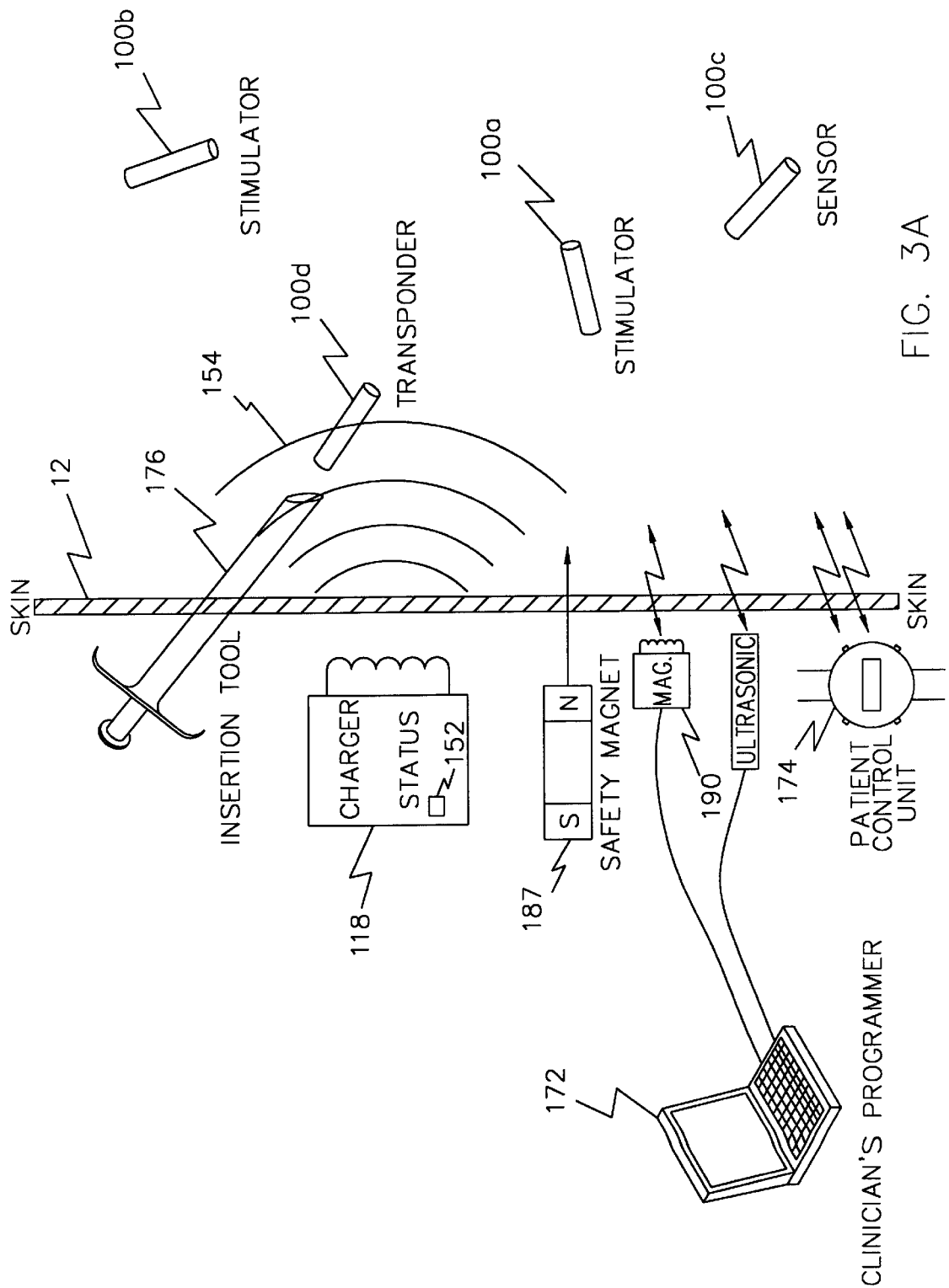

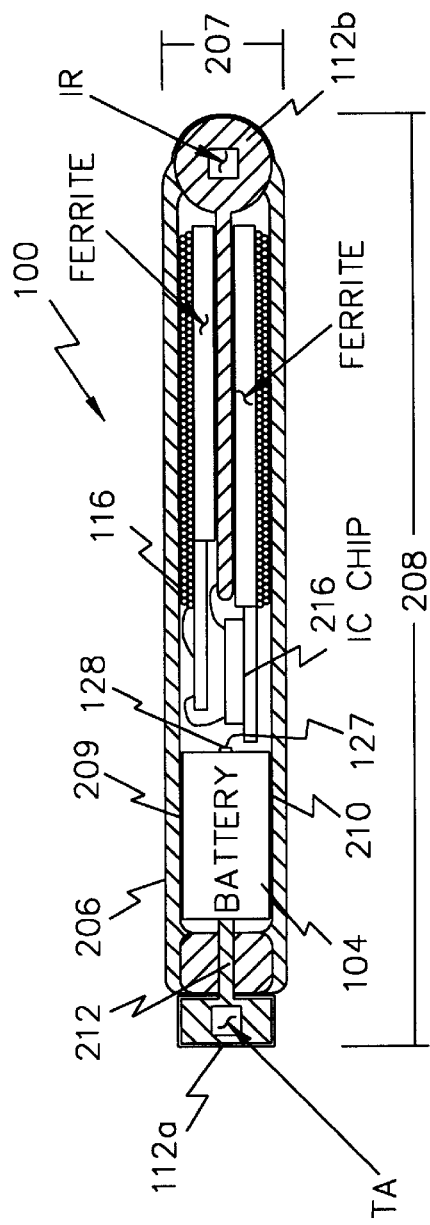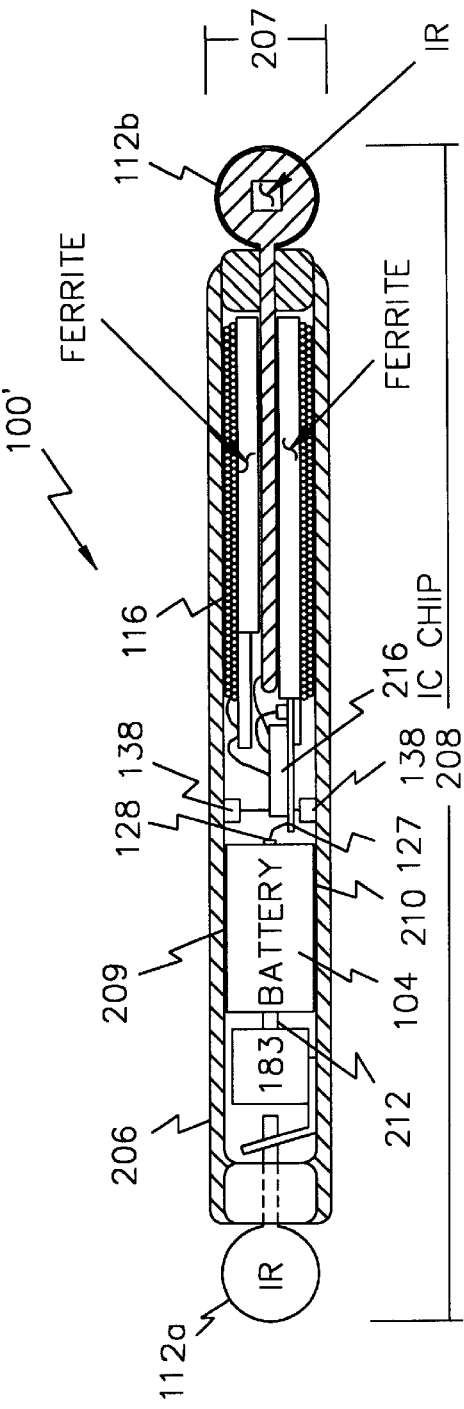
FIG. 5A
FIG. 5B

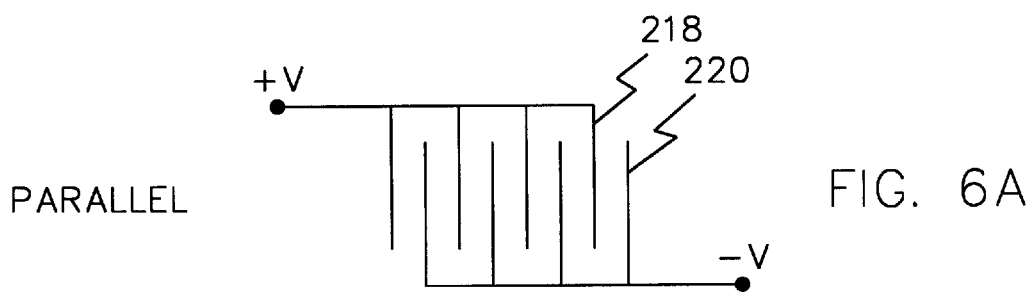
PARALLEL  FIG. 6A
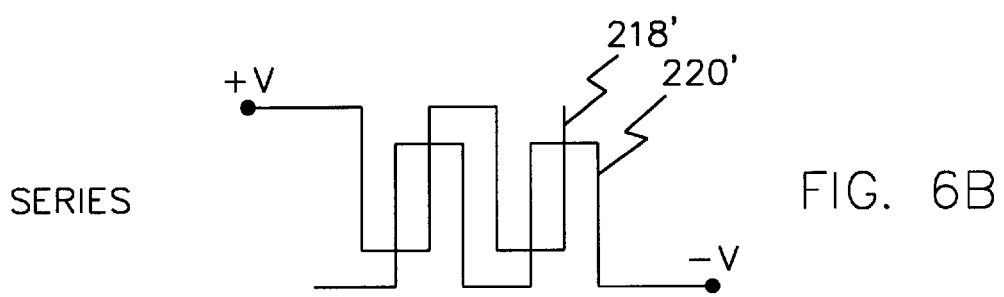
SERIES  FIG. 6B
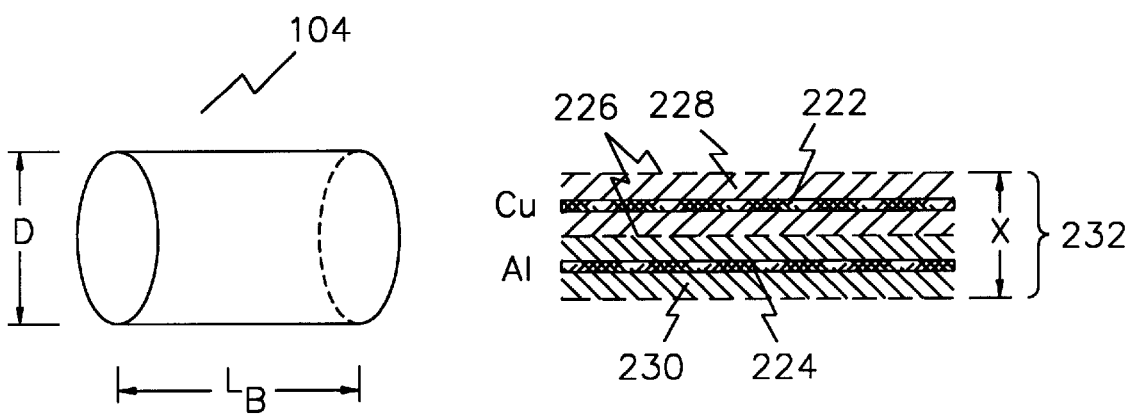
FIG. 7A  FIG. 7B

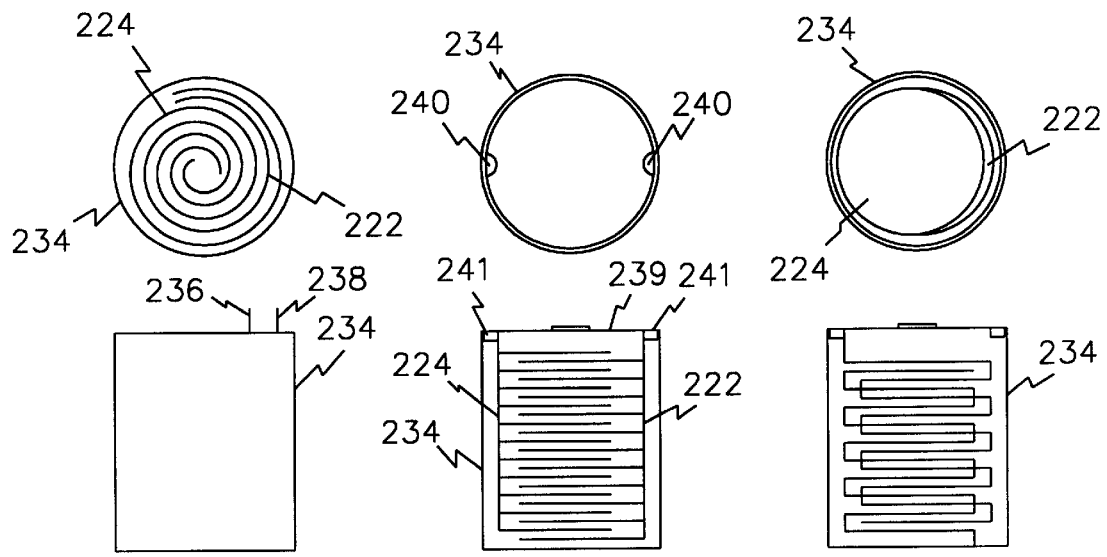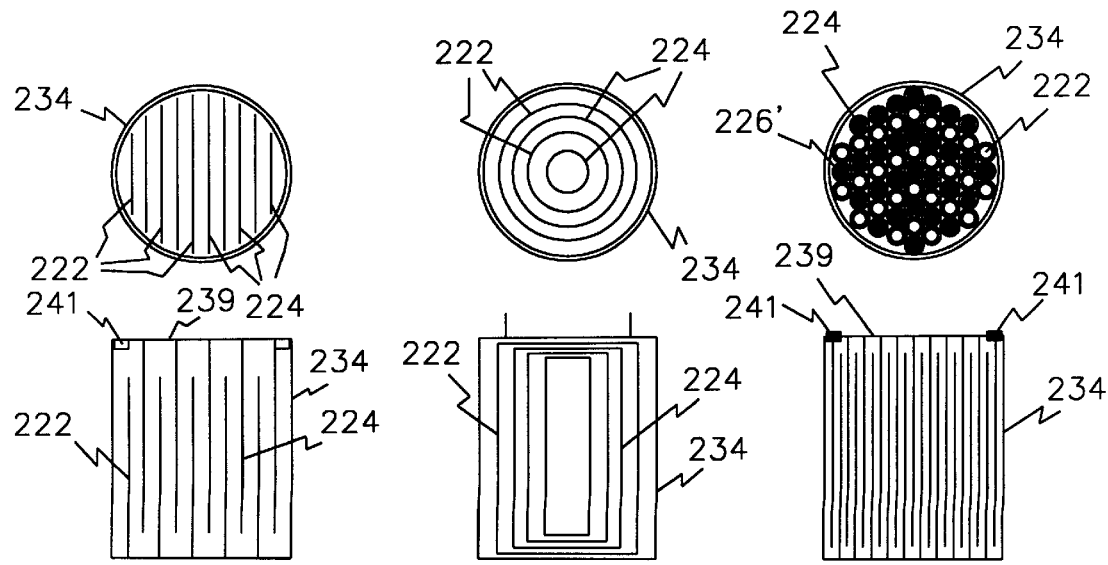
FIG. 8A  FIG. 8B  FIG. 8C
FIG. 8D  FIG. 8E  FIG. 8F

BATTERY-POWERED PATIENT IMPLANTABLE DEVICE

This application claims the benefit of U.S. Provisional Application No. 60/039,164 filed Feb. 26, 1997.

BACKGROUND OF THE INVENTION

The present invention relates to devices configured for implanting beneath a patient's skin and more particularly to such devices incorporating a battery for powering electronic circuitry for various purposes including tissue, e.g., nerve or muscle, stimulation and/or parameter monitoring and/or data communication.

Implantable devices for tissue stimulation (i.e., microstimulators) are known in the art. See, e.g., U.S. Pat. Nos. 5,193,539; 5,193,540; 5,312,439; 5,324,316; 5,358,514; 5,405,367; 5,571,148, which are incorporated herein by reference.

Such known microstimulators are characterized by a sealed housing which contains electronic circuitry for producing small electric currents between spaced electrodes. By precisely implanting the microstimulators proximate to targeted tissue, the currents will stimulate the nerve to produce medically beneficial results.

Typically, such prior microstimulators derive operating power from an internal coil that is inductively coupled to an external AC magnetic field produced, for example, by a drive coil mounted proximate to the microstimulator. An AC voltage induced in the internal coil is rectified and filtered to produce a DC operating voltage which is used to power the electronic circuitry. Such an arrangement requires that the user remain in close proximity to the drive coil to maintain tissue stimulation.

SUMMARY OF THE INVENTION

The present invention is directed to a device configured for implanting beneath a patient's skin for the purpose of tissue, e.g., nerve or muscle, stimulation and/or parameter monitoring and/or data communication. Devices in accordance with the invention are comprised of a sealed housing, preferably having an axial dimension of less than 60 mm and a lateral dimension of less than 6 mm, containing a self-contained power source capable of supplying at least 1 microwatt-hour to power consuming circuitry for actuating an input/output transducer. The circuitry in each device is preferably remotely addressable and includes a data signal receiver and a device controller.

Depending upon the intended application of the device, the power consuming circuitry can be designed to demand a high load current for a relatively short interval, e.g., for bladder stimulation, or a lower load current for a much longer interval or continuously, e.g., for bone growth stimulation. In accordance with the invention, a power source in accordance with the invention has a capacity of at least 1 microwatt-hour which for a typical application is able to power the circuitry for over one hour, thus liberating the user from having to be continuously coupled to an external field generator.

In accordance with a significant aspect of the invention, the power source comprises a battery, preferably formed by a pair of conductive plates having electrolyte disposed therebetween. The battery is preferably physically configured to minimize eddy current formation.

In accordance with a preferred embodiment of the invention, a charging circuit is provided for recharging the battery. The charging circuit is capable of producing a charging current in response to an externally produced AC magnetic field.

In a further aspect of the present invention, an external charger is used to periodically generate an AC magnetic field for supplying energy to the aforementioned charging circuit and one preferred embodiment includes means for generating a data signal representative of the status of the battery to the external charger.

In accordance with a still further aspect of the invention, an identification address is stored in each implantable device used in a system, thus enabling individual device, to be addressed. That is, the data signal receiver in each device will respond to a data signal identifying the address stored by that device to actuate the device input/output transducer.

The input/output transducer in accordance with the invention preferably comprises at least one electrode. When used for nerve stimulation, the controller supplies a sequence of drive pulses to the electrode to stimulate adjacent nerves. When used for parameter monitoring, the electrode is used to monitor an electrical signal indicative of certain body conditions.

In accordance with a significant feature of preferred embodiments of the invention, each implantable device can be individually addressed and programmed to selectively operate in one or more of the following modes: (1) stimulation, (2) monitoring, and/or (3) communication.

The novel features of the invention are set forth with particularity in the appended claims. The invention will be best understood from the following description when read in conjunction with the accompanying drawings.

BRIEF DESCRIPTION OF THE DRAWINGS

FIG. 3A is a simplified functional block diagram of the use of the implanted devices of the present invention (microstimulators, microsensors and microtransponders) in an environment where they are recharged and controlled from devices external to a patient's body;

FIG. 5A shows a side view of a battery-powered implanted device, e.g., a microstimulator, made in accordance with the present invention;

FIG. 5B shows a side view of another implantable battery-powered device, one employing an internal coupling capacitor, made in accordance with the invention;

FIGS. 6A and 6B conceptually illustrate parallel and series connections, respectively, of the electrodes used within a battery of a preferred implantable device;

FIG. 7A illustrates the general cylindrical shape of the battery used within the preferred implantable device of the present invention;

FIG. 7B conceptually depicts the basic electrode pair used within the battery of the implantable device of the present invention;

FIGS. 8A–8G illustrate various configurations of electrode wrapping, stacking, interleaving, or other positioning of the basic electrode pair that may be used within a cylindrical shaped battery of the present invention;

DESCRIPTION OF THE PREFERRED EMBODIMENTS

The present invention is directed to a device configured for implanting beneath a patient's skin for the purpose of tissue, e.g., nerve or muscle, stimulation and/or parameter monitoring and/or data communication. Devices in accordance with the invention are comprised of a sealed housing, preferably having an axial dimension of less than 60 mm and a lateral dimension of less than 6 mm, containing a power source and power consuming circuitry including a controller, an address storage means, a data signal receiver and an input/output transducer. When used as a stimulator, such a device is useful in a wide variety of applications to stimulate nerves and associated neural pathways, e.g., to decrease or relieve pain, stimulate specific muscles or organs to better carry out a body function (e.g., to exercise weak or unconditioned muscles or to control urinary incontinence), and the like. Preferably microstimulators of the present invention are individually addressable for control purposes via a magnetic, RF or ultrasonic signal.

Figure 1:
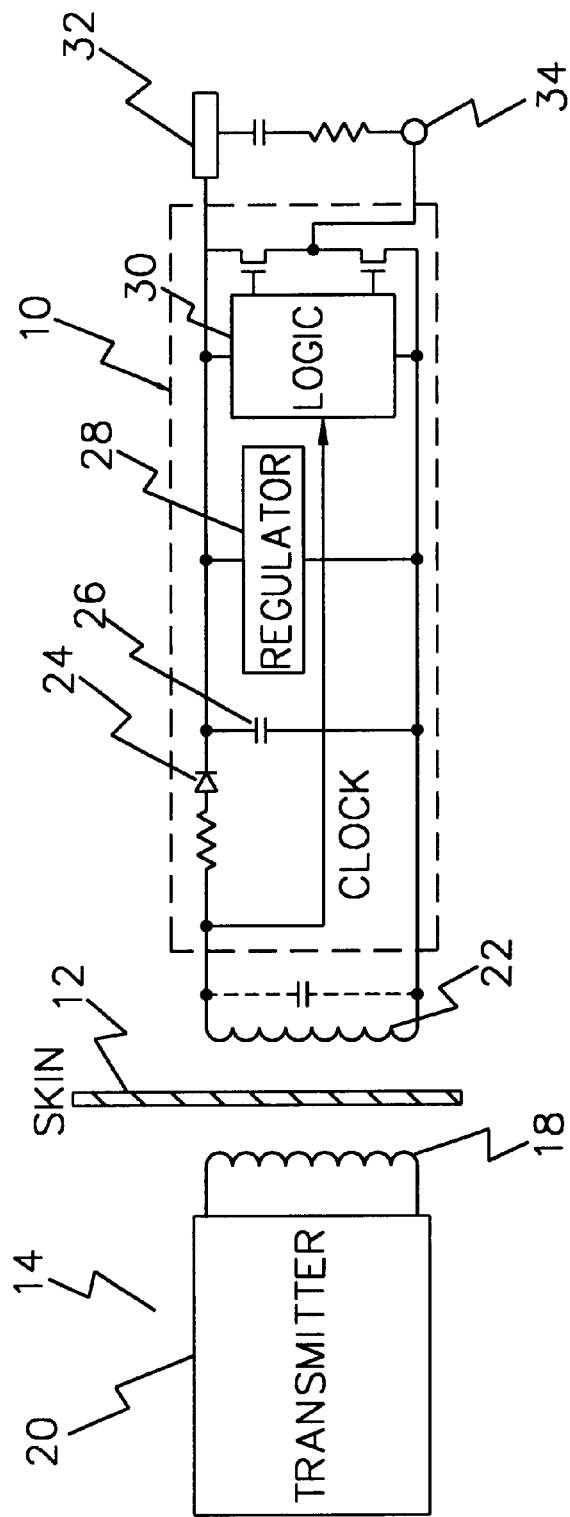
FIG. 1 illustrates a block diagram of a microstimulator as known in the prior art.

FIG. 1 shows an exemplary prior art implantable stimulator 10 (as shown in FIG. 1 of the aforementioned U.S. Pat. No. 5,312,439) implanted beneath a patient's skin 12 that receives power from an externally located power supply 14 via an alternating magnetic field generated by an externally mounted coil 18 that is energized by a transmitter 20. Within the stimulator 10, the magnetic field generates an AC current in a coil 22 that is rectified by rectifier 24 and stored in a capacitor 26 in conjunction with a regulator 28 to generate a voltage that powers its logic 30. The logic 30 is then used to generate a stimulation current between electrodes 32 and 34. Since the control logic 30 relies upon power stored in the capacitor 26 to supply its operating power, it typically stops functioning in a short period of time after the external power supply 14 is removed as the charge stored in capacitor 26 is depleted. Consequently, when such a stimulator 10 is used in an application which requires continuous stimulation, e.g., for blocking pain in a neural pathway, the continuous presence and activation of the external power supply 14 is required. While such a continuous presence can be achieved by use of a portable power supply, its physical presence can be considered as a life style limitation.

Figure 2:
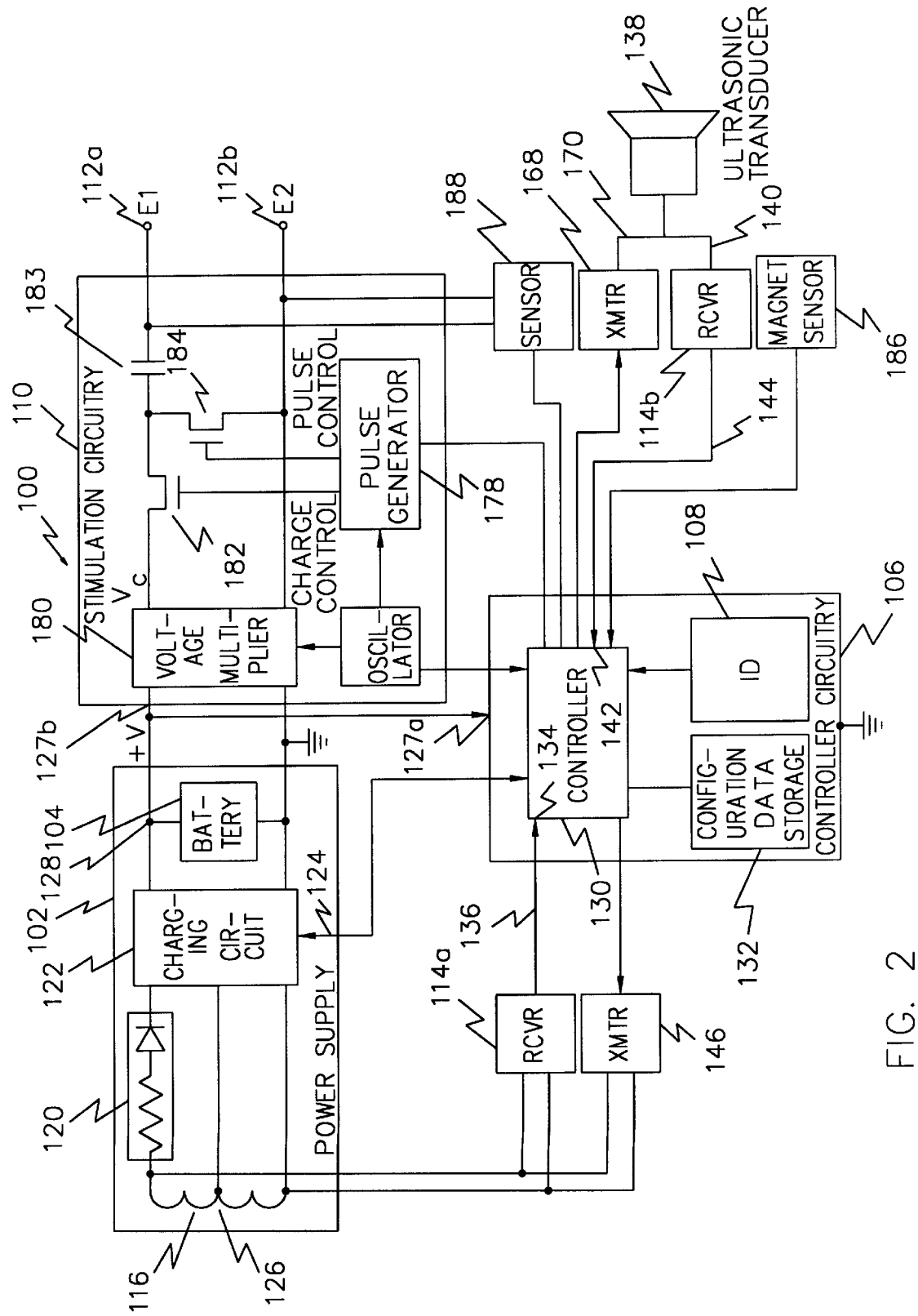
FIG. 2 comprises a block diagram of the device of the present invention including a battery for powering the device for a period of time in excess of one hour in response to a command from an external controller.

In contrast, FIG. 2 shows a block diagram of an electrically-powered implantable device 100 of the present invention (configured as a microstimulator) that can stimulate tissue (e.g., a neural pathway or nerve) for a prolonged period of time, i.e., in excess of one hour, without requiring the continuous use of an external power source. Consequently, in an exemplary application, a preferred microstimulator 100 can be used to block pain in a selected nerve for a prolonged period of time, long after the external power source has been removed. The microstimulator 100 of the present invention is comprised of a sealed housing 206 (see FIG. 5) for enclosing a power source 102, e.g., a rechargeable battery 104, and power consuming electronic circuitry including (1) controller circuitry 106 powered by the power source 102 and having address storage circuitry 108 with an identification address (ID) stored within, (2) stimulation circuitry 110 powered by the power source 102 and operating under control of the controller circuitry 106 for providing drive pulses to one or more electrodes (i.e., transducers) 112, and (3) receiver means 114 for providing command and address identification information to the controller circuitry 106.

In a preferred implementation, the power source 102 comprises a rechargeable battery 104 used in conjunction with a charging circuit to provide sufficient power for prolonged activation of the controller circuitry 106 and the stimulation circuitry 110. However, embodiments of the present invention alternatively use a primary battery in place of the rechargeable battery 104, e.g., in applications where a treatment regimen is relatively short term and thus, the power requirements are within the power capacity of the primary battery.

In operation, a coil 116 receives power in the form of an alternating magnetic field generated from an external power source 118 (see FIG. 3A) and responsively supplies an AC current to a rectifier 120 which is passed as a rectified DC current to a charging circuit 122. The charging circuit 122 then monitors the voltage V on battery 104 and charges it according to its preferred charging characteristics (current and voltage). As discussed further below, the charging circuit 122 preferably communicates via path 124 with the controller circuitry 106 which in turn periodically communicates with the external power source 118 via a magnetic, ultrasonic, or RF signal.

In a typical application (see FIG. 3A), a plurality of such devices 100, e.g., microstimulators, are implanted under the skin 12 of a patient's body and simultaneously subjected to an alternating magnetic field 154 from the external power source 118. Accordingly, once the charging circuit 122 determines that battery 104 has been sufficiently charged, the charging circuit preferably detunes coil 116, e.g, by shunting out centertap 126 (or adding a capacitor across the coil), and thus minimizes any heat generation in the charging circuit 122 or in the battery 104 from overcharging. Thus, the external power source 118 can continue to provide charging power via an alternating magnetic field indefinitely. However in one preferred embodiment, the external power source periodically polls the implanted devices for status information and continues to provide charging power until it has received status information from each of the implanted devices 100 that its battery 104 is charged.

Both the controller circuitry 106 (via power input terminal 127a) and stimulation circuitry 110 (via power input terminal 127b) receive power from the battery 104 power output terminal 128. The power dissipation of circuitry within the implanted device 100 is minimized by the use of CMOS and other lower power logic. Accordingly, the required capacity of the battery 104 is minimized.

The controller circuitry 106 controls the operation of the stimulation circuitry 110 using a controller 130 (preferably a state machine or microprocessor) according to configuration data within a configuration data storage 132 coupled to controller 130. The configuration data specifies various programmable parameters (discussed further below) that effect the characteristics of the drive pulses generated by stimulation circuitry 110 as controlled by the controller 130. Preferably, each implanted device 100, e.g., microstimulator, can be actuated (enabled/disabled) or have its characteristics altered via communications with one or more devices external to itself. Accordingly, each implanted device 100 uses its address storage 108, e.g., an EEPROM, PROM, or other nonvolatile storage device programmed during manufacture, to identify itself (e.g., using an ID code stored within of 8 or more bits). Alternatively, the address storage 108 can be comprised of a portion of an integrated circuit that is mask programmed to form all or a portion of the ID and/or the use of a laser trimming process to designate all or the remaining portion of the ID. In a further alternative implementation, the ID can be designated by a selection of jumpers, e.g., wire bonds, used individually or in combination with the use of a laser trimming process. In operation, an external device (e.g., charger 118) transmits a modulated magnetic, ultrasonic, or RF command signal containing command information that includes an address field. When the implanted device 100 receives and demodulates this command signal to receive the command information within, it first determines whether there is a match to its address within its address storage 108 before processing the rest of its data. Otherwise, the command information is ignored.

In a first embodiment, alternating magnetic field 154 is amplitude modulated with this command signal. Receiver circuitry 114a detects and demodulates this command signal by monitoring the signal generated across coil 116 (preferably the same coil used for charging the rechargeable battery 104). The demodulated data is provided to a controller data input 134 via path 136 where its applicability to a particular implanted device 100 is determined. Alternatively, the command signal can modulate an RF signal which can be detected in a similar manner by receiver 114a (configured to demodulate an RF signal) using coil 116 as an antenna or using a separate antenna.

In a next embodiment, an ultrasonic signal can be used to deliver this command signal to each implanted device 100. In this embodiment, an ultrasonic transducer 138 located within the device 100 generates a signal 140 which is demodulated by ultrasonic demodulator 114b. This demodulated signal is then provided to an ultrasonic data input 142 via path 144 and processed in a manner similar to that described in reference to a magnetic signal. The ultrasonic implementation provides significant advantages in that a patient's body is primarily comprised of fluid and tissue that is conducive to passing an ultrasonic signal. Consequently, a control device located anywhere inside (or external but in contact with) the patient's body can communicate with each device 100 implanted within.

Figure 3B:
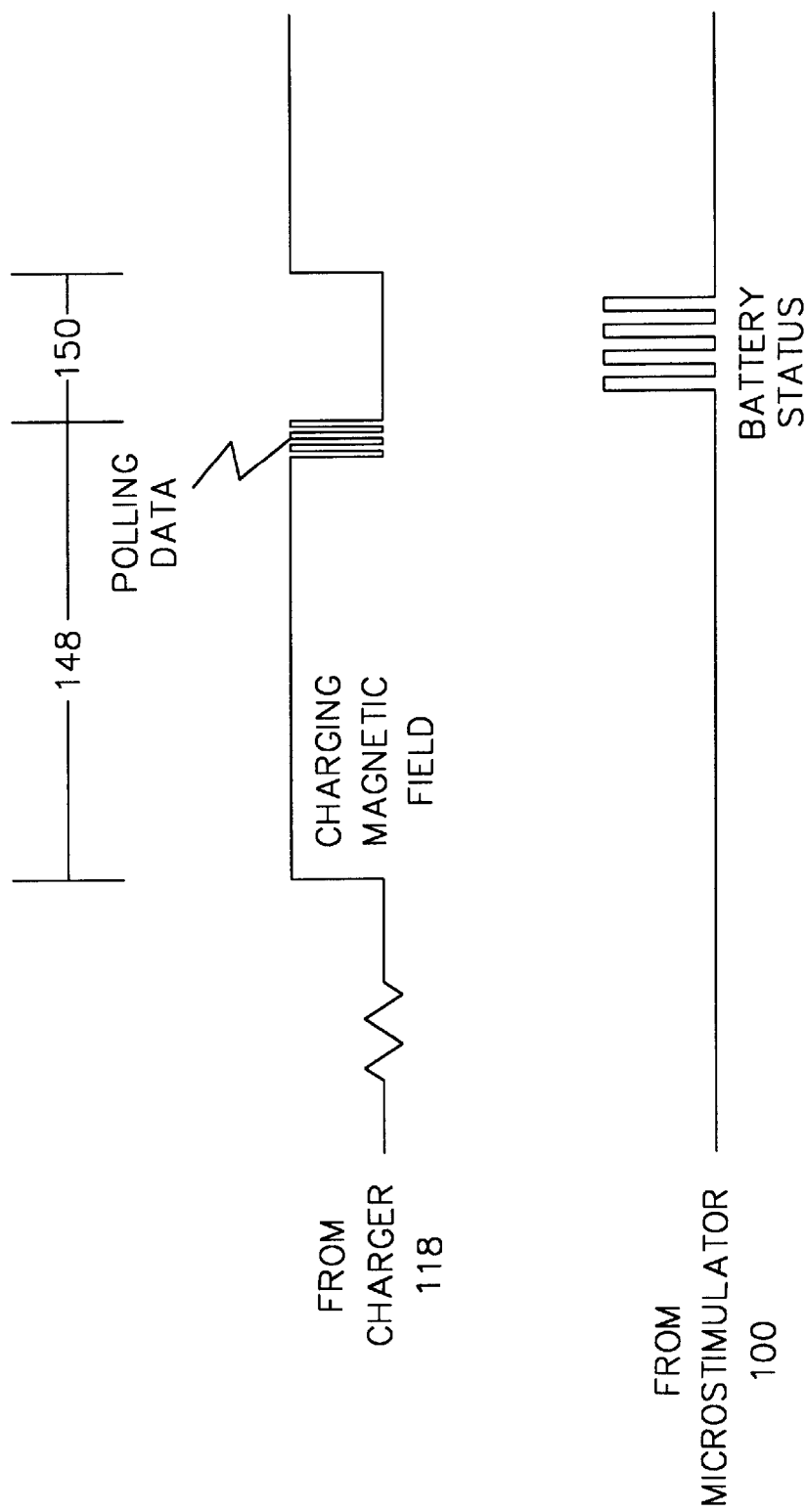
FIG. 3B shows a simplified timing diagram showing periodic breaks in the generation of the charging magnetic field to selectively interrogate the battery status of the implanted devices.

In a preferred embodiment, the implanted device 100 includes means for transmitting status and data to external devices. In an exemplary charging mode, it is preferable that each device 100 can individually communicate with charger 118 so that charger 118 can determine when all of the implanted devices 100 have been fully charged. Preferably, device 100 includes transmitter means to emit a magnetic signal modulated with this data. This transmitter means comprises modulator circuitry 146 which amplitude modulates an AC voltage and delivers this modulated signal to coil 116 which emits a modulated magnetic signal. While this modulated signal can use a different carrier frequency from that of the AC signal used by the charger 118, it is preferable that the communication channel, i.e., the magnetic field 154 between the devices, be time-shared as shown in FIG. 3B. In FIG. 3B, the charger 118 emits an alternating magnetic field for a first time period 148. At the end of the first time period 148, this alternating magnetic field is modulated (e.g., amplitude modulated) with a series of bits corresponding to polling data corresponding to a selected microstimulator 100 (i.e., including an address for one implanted device). The charger 118 then goes into a receive mode for a second time period 150 during which time the selected device 100 emits a magnetic signal modulated with a series of bits corresponding to its battery status. This charging/polling cycle preferably repeats for all of the implanted devices within the operational range of the charger 118. Once the charger 118 determines that all of the devices 100 have been charged, the cycle is terminated and the patient or clinician is preferably notified, e.g., using a visual or audio annunciator 152.

Alternatively, ultrasonic means can be used to communicate status or other data from the implanted device 100 to an external device. In such an embodiment, an ultrasonic transmitter 168 under control of the controller 130 generates a modulated signal on line 170 that is emitted by ultrasonic transducer 138. As previously discussed, an ultrasonic signal efficiently passes through the body fluids and tissues and as such is a preferred communication means for communication between devices implanted within the patient's body, e.g., other microstimulators 100, and suitable for communication with external devices in contact with the patient's skin.

The use of magnetic or ultrasonic communication, i.e., transmitter and receiver, means are not mutually exclusive and in fact a preferred implanted device includes both. For example as shown in FIG. 3A, a clinician's programmer 172 (a device for primarily programming the operation of the implanted devices 100), can communicate with a microstimulator 100a using a modulated magnetic signal from magnetic emitter 190 and periodically receive a modulated magnetic signal from microstimulator 100a reflecting its battery status. While this magnetic means of communication is preferable during a charging mode, a patient control unit 174 (e.g., a device in direct contact with the skin, typically in the form of a "wrist watch", primarily used for monitoring the status of the embedded devices 100) will preferably communicate using ultrasonic means. Additionally, communication between implanted microstimulators 100 is also desirable, e.g., in a master-slave or transponder-slave configuration. For these modes, ultrasonic means are preferable since ultrasonic signals efficiently pass through the body fluids.

The battery-powered device 100 of the present invention is preferably configurable to operate in a plurality of operation modes, e.g., via a communicated command signal. Alternatively, preconfigured, battery-powered, implanted devices are also considered to be within the scope of the present invention. In a first operation mode, device 100 (sized so that it can be implanted using a hypodermic needle type insertion tool 176) is configured to be a stimulator, hence such a device is referred to as a microstimulator (e.g., 100a and 100b). In this embodiment, the controller 130 commands stimulation circuitry 110 to generate a sequence of drive pulses through electrodes 112 to stimulate tissue, e.g., a nerve, proximate to the implanted location of the microstimulator 100a or 100b. In operation, a programmable pulse generator 178 and voltage multiplier 180 are configured with parameters (see Table I) corresponding to a desired pulse sequence and specifying how much to multiply the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby nerve. Alternatively, as disclosed in the previously incorporated references, electrodes can be selected that will form an equivalent capacitor within the body tissue.

TABLE I

Stimulation Parameters

| | |
|---|---|
| Current: | Continuous current charging of storage capacitor |
| Charging currents: | 1, 3, 10, 30, 100, 250, 500 μa |
| Current Range: | 0.8 to 40 ma in nominally 3.2% steps |
| Compliance Voltage: | selectable, 3–24 volts in 3 volt steps |
| Pulse Frequency (PPS): | 1 to 5000 PPS in nominally 30% steps |
| Pulse Width: | 5 to 2000 μs in nominally 10% steps |
| Burst On Time (BON): | 1 ms to 24 hours in nominally 20% steps |
| Burst Off Time (BOF): | 1 ms to 24 hours in nominally 20% steps |
| Triggered Delay to BON: | either selected BOF or pulse width |
| Burst Repeat Interval: | 1 ms to 24 hours in nominally 20% steps |
| Ramp On Time: | 0.1 to 100 seconds (1, 2, 5, 10 steps) |
| Ramp Off Time: | 0.1 to 100 seconds (1, 2, 5, 10 steps) |

While the desirability of being able to stimulate tissue for a prolonged period of time has been described, failure modes can also be envisioned. Therefore, a magnet sensor 186 (preferably a semiconductor, e.g., Hall-effect, sensor) is preferably coupled to the controller 130 which can be used to modify the function, e.g., discontinue operation, of the microstimulator 100 when exposed to a static magnetic field. Such a magnet sensor 186 can be activated by placing a safety magnet 187 (to generate the static magnetic field) proximate to the microstimulator 100 at the patient's skin 12. Additionally, it is desirable that a microstimulator 100 cease operation when its battery voltage reaches a lower limit (or exceeds a maximum temperature) as determined by the charging circuitry 122 and communicated to the controller circuitry 106. This ensures reliable operation as well as prolonging the useful life of the rechargeable battery 104. When this low voltage condition is detected, a preferred device periodically emits a corresponding status signal (preferably in response to remotely generated interrogation/polling signal) to request that the battery be recharged.

In a next operation mode, the battery-powered implantable device 100 can be configured to operate as a sensor, i.e., a microsensor 100c, that can sense one or more physiological or biological parameters in the implanted environment of the device. In a preferred mode of operation, a system controller, e.g., an externally located device or an implanted device, periodically request the sensed data from each microsensor 100c using its ID stored in address storage 108, and responsively sends command signals to microstimulators, e.g., 100a and 100b, adjusted accordingly to the sensed data. For example, a sensor 188 can be coupled to the electrodes 112 to sense or otherwise used to measure a biological parameter, e.g., temperature, glucose level, or $O_2$ content. Additionally, the ultrasonic transducer 138 or the coil 116 can be used to respectively measure the magnetic or ultrasonic signal magnitudes (or transit durations) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operation mode, the battery-powered implantable device 100 can be configured to operate as a transponder, i.e., a microtransponder 100d. In this operation mode, the microtransponder receives (via the aforementioned receiver means, e.g., magnetic or ultrasonic) a first command signal from a system controller and retransmits this signal (preferably after reformatting) to other implanted devices (e.g., microstimulators, microsensors, and/or microtransponders) using the aforementioned transmitter means (e.g., magnetic or ultrasonic). While a microtransponder may receive one mode of command signal, e.g., magnetic, it may retransmit the signal in another mode, e.g., ultrasonic. For example, clinician's programmer 172 may emit a modulated magnetic signal using a magnetic emitter 190 to program/command the implanted devices. However, the magnitude of the emitted signal may not be sufficient to be successfully received by all of the implanted devices. As such, a microtransponder 100d may receive the modulated magnetic signal and retransmit it (preferably after reformatting) as a modulated ultrasonic signal which can pass through the body with fewer restrictions. In another exemplary use, the patient control unit 174 may need to monitor a microsensor 100c in a patient's foot. Despite the efficiency of ultrasonic communication in a patient's body, an signal could still be insufficient to pass from a patient's foot to a patient's wrist (the typical location of the patient control unit 174). As such, a microtransponder 100d could be implanted in the patient's torso to improve the communication link.

In still another operation mode, a battery-powered device can be configured to operate as a master system controller that can alter the operation of the other implanted devices, i.e., microstimulators and microsensors, in a closed loop mode of control.

Figure 4:
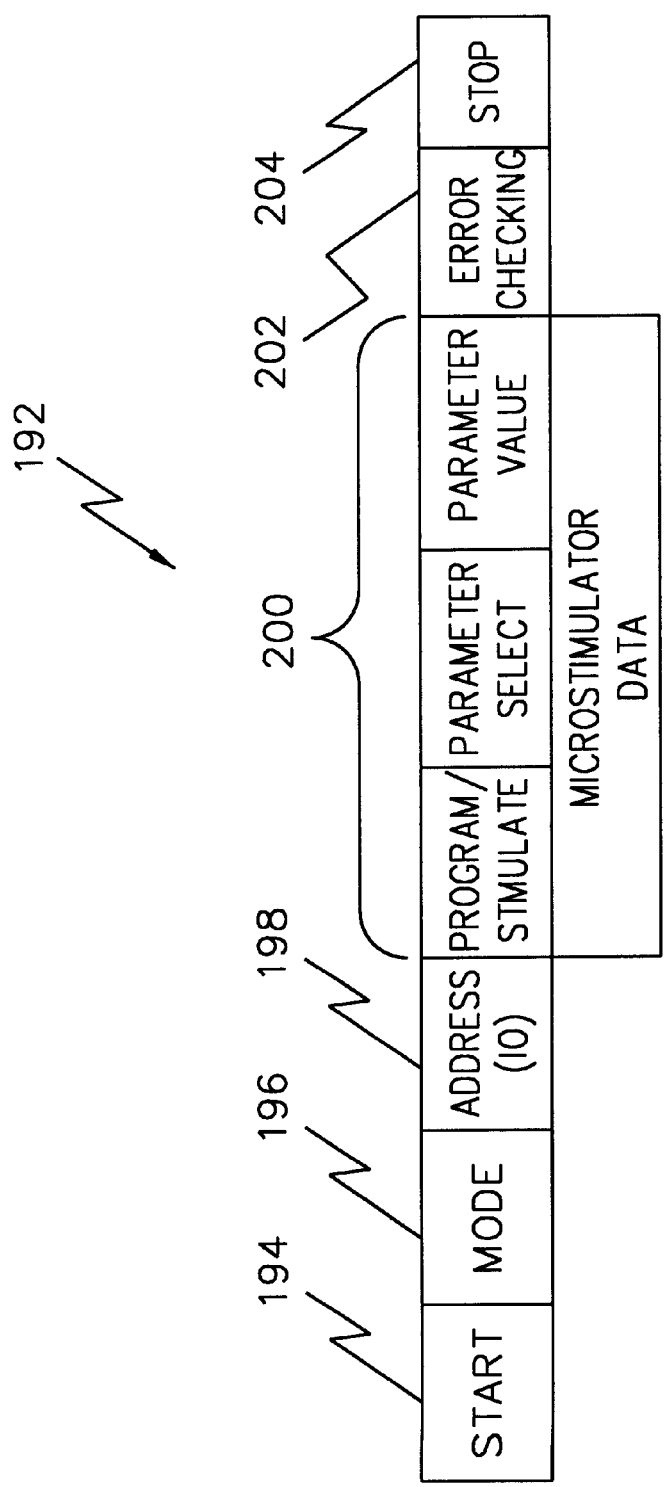
FIG. 4 is a simplified diagram showing the basic format of data messages for commanding/interrogating the implanted microstimulators, microsensors and microtransponders of the present invention.

FIG. 4 shows the basic format of an exemplary message for communicating with the aforementioned battery-powered devices 100, all of which are preconfigured with an address (ID), preferably unique to that device, in their identification storage 108 to operate in one or more of the following modes (1) for nerve stimulation, i.e., as a microstimulator, (2) for biological parameter monitoring, i.e., as a microsensor, and/or (3) for retransmitting received signals after reformatting to other implanted devices, i.e., as a microtransponder. The command message 192 is primarily comprised of a (1) start portion 194 (one or more bits to signify the start of the message and to synchronize the bit timing between transmitters and receivers, (2) a mode portion 196 (designating the operating mode, e.g., stimulator, sensor, transponder, or group mode), (3) an address (ID) portion 198 (corresponding to either the identification address 108 or a programmed group ID), (4) a data field portion 200 (containing command data for the prescribed operation), (5) an error checking portion 202 (for ensuring the validity of the message 192, e.g., by use of a parity bit), and (6) a stop portion 204 (for designating the end of the message 192). The basic definition of these fields are shown below in Table II. Using these definitions, each device can be separately configured, controlled and/or sensed as part of a system controlling one or more neural pathways within a patient's body.

TABLE II

Message Data Fields

| MODE | ADDRESS (ID) |
| --- | --- |
| 00 = Stimulator | 8 bit identification address |
| 01 = Sensor | 8 bit identification address |
| 02 = STransponder | 4 bit identification address |
| 03 = SGroup | 4 bit group identification address |

Data Field Portion

| | | |
| --- | --- | --- |
| Program/Stimulate Parameter/ Preconfiguration Select | = | select operating inode |
| | = | select programmable parameter in program mode or preconfigured stimulation or sensing parameter in other modes |
| Parameter Value | = | program value |

Additionally, each device 100 can be programmed with a group ID (e.g., a 4 bit value) which is stored in its configuration data storage 132. When a device 100, e.g., a microstimulator, receives a group ID message that matches its stored group ID, it responds as if the message was directed to its identification address 108. Accordingly, a plurality of microstimulators, e.g., 100a and 100b, can be commanded with a single message. This mode is of particular use when precise timing is desired among the stimulation of a group of nerves.

FIG. 5A shows a side view of a microstimulator 100 made in accordance with the present invention which includes battery 104 for powering the circuitry within. The battery 104 conveniently fits within a sealed elongate housing 206 (preferably hermetically sealed) which encases the microstimulator 100. In a preferred device 100, the axial dimension 208 is less than 60 mm and the lateral dimension 207 is less than 6 mm.

For the embodiment shown in FIG. 5A, the battery 104 is preferably housed within its own battery case 209, with the battery terminals comprising an integral part of its case 209 (much like a conventional AA battery). Thus, the sides and left end of the battery 104 (as oriented in FIG. 5A) may comprise one battery terminal 210, e.g., the negative battery terminal, and the right end of the battery 104 may comprise the other battery terminal, e.g., the positive battery terminal used as the output terminal 128. Advantageously, because such a battery case 209 is conductive, it may serve as an electrical conductor for connecting an appropriate circuit node for the circuitry within the microstimulator 100 from one side of the battery to the other. More particularly, for the configuration shown in FIG. 5A, the battery terminal 210 may serve as a ground point or node for all of the circuitry housed within the device housing 206. Hence, stem 212 from the electrode 112a on the left end of the microstimulator 100, which from an electrical circuit point of view is simply connected to circuit ground, may simply contact the left end of the battery 104. Then, this same circuit ground connection is made available near or on the rim of the battery 104 on its right side, near one or more IC chips 216 (preferably implementing the device's power consuming circuitry, e.g., the controller 106 and stimulation circuitry 110) on the right side of battery 104 within the right end of the housing 206. By using the conductive case 209 of the battery 104 in this manner, there is no need to try to pass or fit a separate wire or other conductor around the battery 104 to electrically connect the circuitry on the right of the device 100 with the electrode 112a on the left side of the device 100.

FIG. 5B shows a battery powered microstimulator 100' that is substantially the same as the device 100 shown in FIG. 5A except that the microstimulator 100' includes internal coupling capacitor 183 (used to prevent DC current flow through the body tissue). The internal coupling capacitor 183 is used for the embodiment shown in FIG. 5B because both of the microstimulator electrodes 112a and 112b used by the microstimulator 100' are made from the same material, iridium. In contrast, the electrodes 112a and 112b for the microstimulator 100 shown in FIG. 5A are made from different materials, and in particular from iridium (electrode 112b) and tantalum (electrode 112a), and such materials inherently provide a substantial capacitance between them, thereby preventing DC current flow. See, e.g., col. 11, lines 26–33, of U.S. Pat. No. 5,324,316.

Figure 5C:
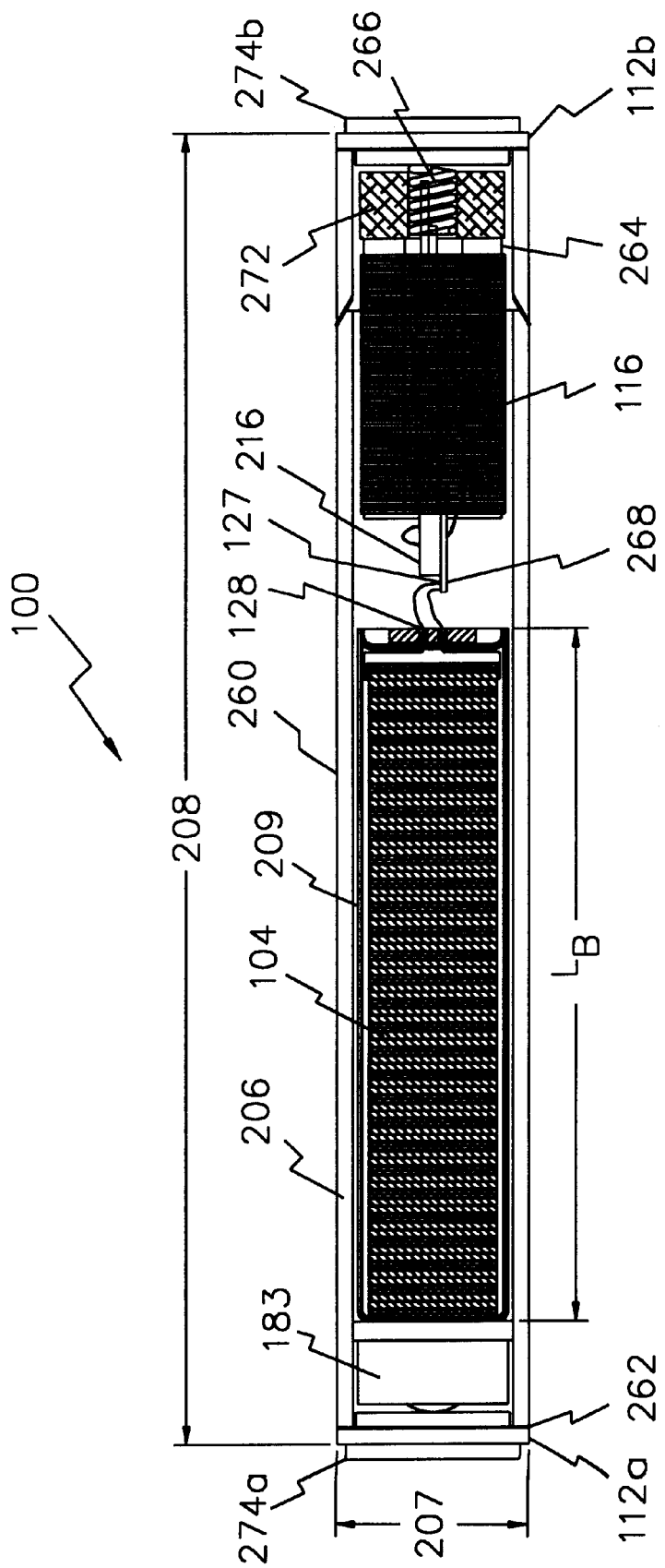
FIGS. 5C and 5D show two side cutaway views of the presently preferred embodiment of an implantable device mounted in a ceramic housing.
Figure 5D:
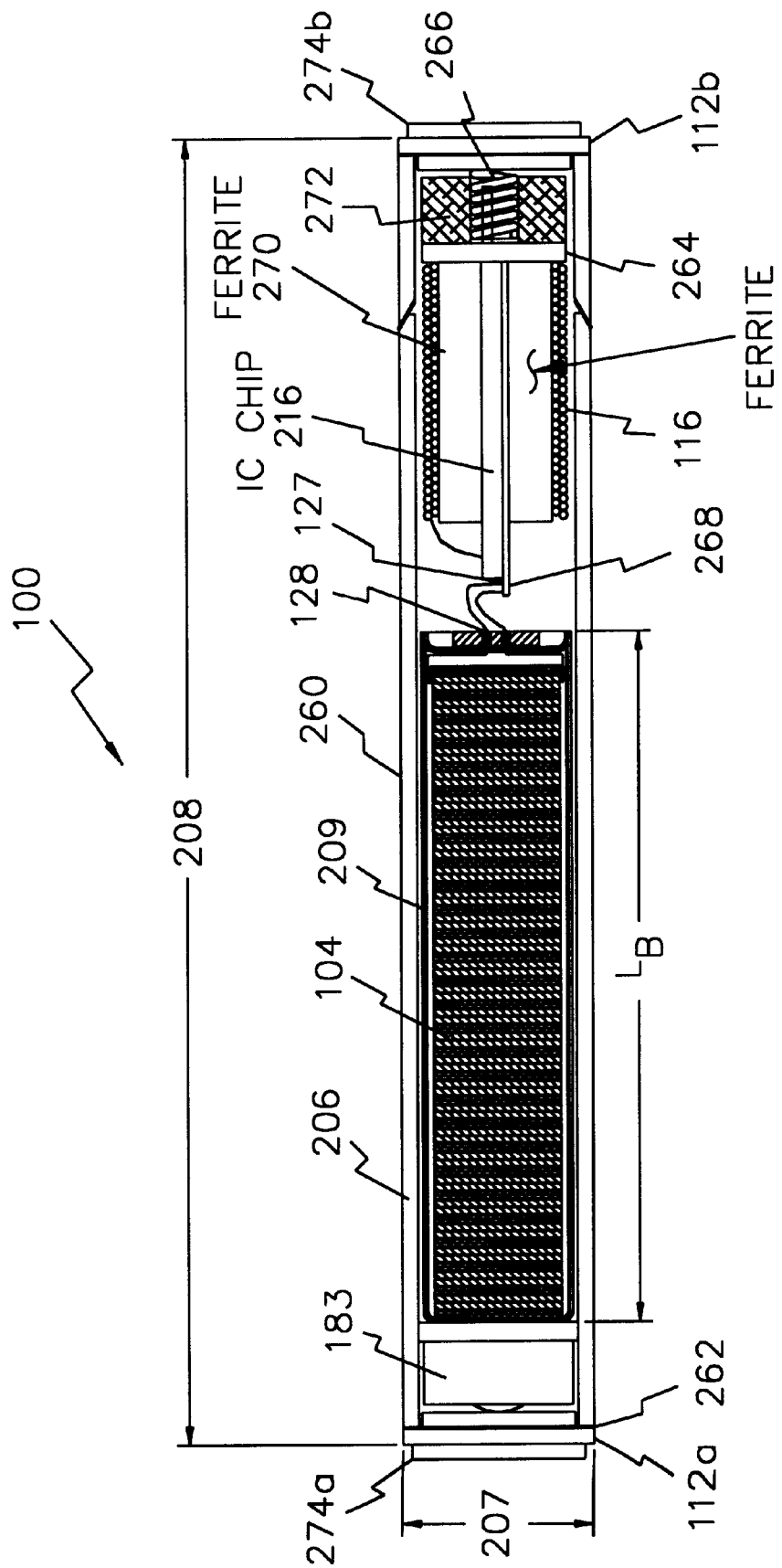

FIGS. 5C and 5D show two side cutaway views of the presently preferred construction of the sealed housing 206, the battery 104, the capacitor 183 and the circuitry (implemented on one or more IC chips 216) contained within. In this presently preferred construction, the housing 206 is comprised of an insulating ceramic tube 260 brazed onto a first end cap forming electrode 112a via a braze 262. At the other end of the ceramic tube 260 is a metal ring 264 that is also brazed onto the ceramic tube 260. The circuitry within, i.e., the capacitor 183, battery 104, IC chips 216, and a spring 266 is attached to an opposing second end cap forming electrode 112b. A drop of conductive epoxy is used to glue the capacitor 183 to the end cap 112a and is held in position by spring 266 as the glue takes hold. Preferably, the IC chips 216 are mounted on a circuit board 268 over which half circular longitudinal ferrite plates 270 are attached. The coil 116 is wrapped around the ferrite plates 270 and attached to IC chips 216. A getter 272, mounted surrounding the spring 266, is preferably used to increase the hermeticity of the device 100 by absorbing water introduced therein. An exemplary getter 272 absorbs 70 times its volume in water. While holding the circuitry and the end cap 112b together, one can laser weld the end cap 112b to the ring 264. Additionally, a platinum, iridium, or platinum-iridium disk or plate 274 is preferably welded to the end caps of the device 100 to minimize the impedance of the connection to the body tissue.

The battery 104 is described more fully below in connection with the description of FIGS. 6–8. Preferably, the battery 104 is made from appropriate materials so as to provide a power capacity of at least 1 microwatt-hour, preferably constructed from a battery having an energy density of about 240 mW-Hr/cm$^3$. A Li—I battery advantageously provides such an energy density. Alternatively, an Li—I—Sn battery provides an energy density up to 360 mW-Hr/cm$^3$. Any of these batteries, or other batteries providing a power capacity of at least 1 microwatt-hour may be used with the present invention.

The battery voltage V of an exemplary battery is nominally 3.6 volts, which is more than adequate for operating the CMOS circuits which are used to implement the IC chip(s) 216, and/or other electronic circuitry, within the device 100. The battery voltage V, in general, is preferably not allowed to discharge below about 2.55 volts, or permanent damage may result. Similarly, the battery 104 should preferably not be charged to a level above about 4.2 volts, or else permanent damage may result. Hence, the aforementioned charging circuit 122 is used to avoid any potentially damaging discharge or overcharge.

Turning next to FIGS. 6–9, additional details concerning the battery 104 used within the implantable device 100 are presented. Basically, the battery 104 may take many forms, any of which may be used so long as the battery can be made to fit within the small volume available. As previously discussed, the battery 104 may be either a primary battery or a rechargeable battery. A primary battery offers the advantage of a longer life for a given energy output but presents the disadvantage of not being rechargeable (which means once its energy has been used up, the device 100 no longer functions). However, for many applications, such as one-time-only muscle rehabilitation regimens applied to damaged or weakened muscle tissue, the device 100, e.g., a microstimulator, need only be used for a short time (after which it can be explanted and discarded, or simply left implanted as a benign medical device). For other applications, a rechargeable battery is clearly the preferred type of energy choice, as the tissue stimulation provided by the microstimulator is of a recurring nature.

The considerations relating to using a rechargeable battery as the battery 104 of the implantable device 100 are presented, inter alia, in the book, *Rechargeable Batteries, Applications Handbook*, EDN Series for Design Engineers, Technical Marketing Staff of Gates Energy Products, Inc. (Butterworth-Heinemann 1992). The basic considerations for any rechargeable battery relate to high energy density and long cycle life. Lithium based batteries, while historically used primarily as a nonrechargeable battery, have in recent years appeared commercially as rechargeable batteries. Lithium-based batteries typically offer an energy density of from 240 mW-Hr/cm$^3$ to 360 mW-Hr/cm$^3$. In general, the higher the energy density the better, but any battery construction exhibiting an energy density resulting in a power capacity greater than 1 microwatt-hour is suitable for the present invention.

One of the more difficult hurdles facing the use of a battery 104 with the device 100 of the present invention relates to the relatively small size or volume inside the housing 206 within which the battery must be inserted. A typical device 100 made in accordance with the present invention will preferably be no larger than about 60 mm long and 6 mm in diameter and includes even smaller embodiments, e.g., 15 mm long with an O.D. of 2.2 mm (resulting in an I.D. of about 2 mm). When one considers that only about ¼ to ½ of the available volume within the device housing 206 is available for the battery, one begins to appreciate more fully how little volume, and thus how little battery storage capacity, is available for the device 100.

Figure 10:
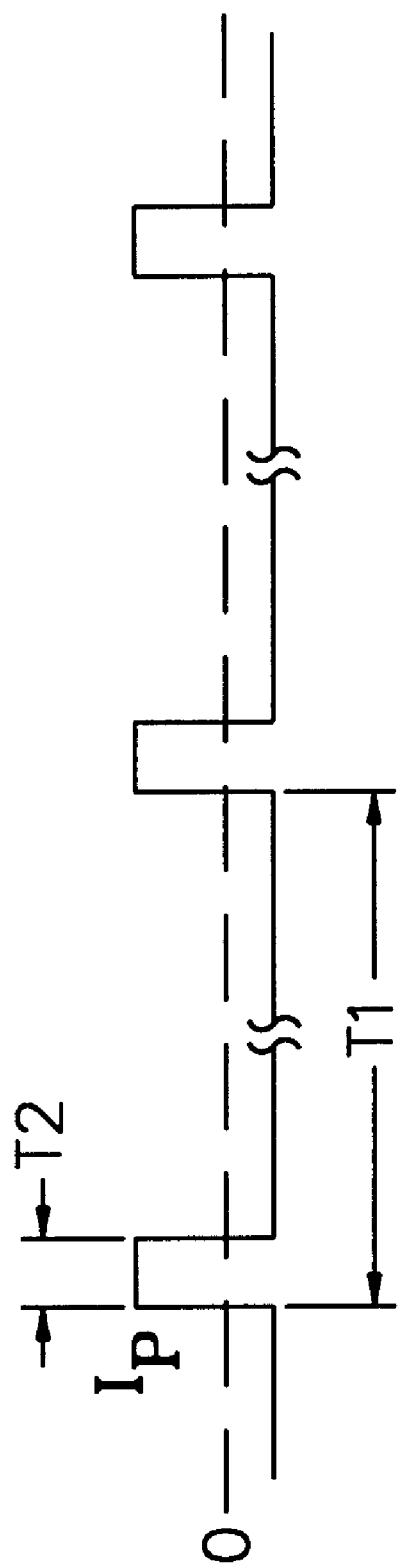
FIG. 10 illustrates an exemplary waveform for drive pulses produced by a preferred microstimulator showing the drive pulse's low duty cycle.

The device 100, e.g., a microstimulator, of the present invention is designed to generally consume only small amounts of power. The principal power drain for power consuming circuitry of the microstimulator 100 is the stimulating current that is applied to the tissue in contact with the electrodes 112. A typical stimulating current is shown in FIG. 10 which exhibits a very low duty cycle. For example, an exemplary waveform for providing an essentially continuous stimulation of a nerve may have 0.2 msec pulses ($T_2$) that occur every 50 msec ($T_1$), i.e., at a 20 Hz rate.

If such current pulses have a peak value of 5 ma ($I_p$), and are delivered at a potential of 3.6 volts (V), then the peak output power (P), in units of watts (W), delivered by the device is P=IV=(5 ma)(3.6 v)=18 mW and the average output power, which is a function of the duty cycle, is P(ave)=18 mW×0.2/50=0.072 mW=72 μW.

If a nominal sized microstimulator is employed, having a length L of 15 mm and an I.D. of 2 mm (so the radius, r, is 1 mm), and assuming that ⅓ of the available length, or 5 mm, is available for the battery ($L_B$), the battery would have a volume of Vol$_{BAT}$=$\pi r^2 L_B$=$\pi$(1 mm)$^2$(5 mm)(1 cm$^3$/1000 mm$^3$)=0.0157 cm$^3$.

Assuming the battery is fabricated from materials that exhibit an energy density of 240 mW-Hr/cm$^3$, it is thus seen that a fully charged battery can support a nominal load of 72 μW (0.072 mW) for a time period of:

(240 mW-Hr/cm$^3$)(0.0157 cm$^3$)/(0.072 mW)=52.3 Hrs which is approximately 2.2 days. If a safety factor of at least two is employed, the battery should thus be recharged each day.

However, other applications may require a significantly smaller drive currents (e.g., 1 μa) albeit at a higher duty cycle, e.g., bone growth stimulation, or possibly larger drive currents (e.g., 40 ma) at a smaller duty cycle, e.g., bladder stimulation or other applications that may only require nerve stimulation for minutes per day. A value of 1 microwatt-hour has been chosen as a minimum specification for a battery used in embodiments of the present invention. However, as shown above, embodiments of the present invention can include batteries with significantly higher capacities and thus such embodiments can encompass a larger range of applications.

Turning next to FIGS. 6A and 6B, the manner in which the battery plates or electrodes may be connected in parallel or in series is illustrated. A parallel connection of interleaved or stacked positive electrodes 218 with negative electrodes 220 is illustrated in FIG. 6A. A series connection of such interleaved electrodes is shown in FIG. 6B. In general, the resistance associated with the parallel connection is lower than the resistance associated with the series connection, which means that the time constant of the battery, i.e., the time it takes to discharge or charge the battery at a given current level, will be higher or longer for the series connection than it is for the parallel connection. While the discharge time constant is generally not of concern for purposes of the present invention (because so little current is drained from the battery when in use), the charge time constant may be important (because that determines, at least in part, how long it takes to recharge the battery).

FIG. 7A depicts a typical cylindrical shape for the battery 104. In general, such shape has a lateral dimension or diameter D and an axial dimension or length $L_B$. However, it is recognized that other shapes are possible and potentially advantageous. For example, a rectangular or prismatic shaped battery can also be used, including ones that may extend the full length of the housing 206, with the power consuming circuitry, e.g., the controller 106 the stimulation circuitry 110, mounted in the surrounding interior areas of the housing 206.

The electrodes used within the battery 104 are arranged in pairs, and have a general relationship as shown in FIG. 7B where the electrodes or plates are mounted in an opposed spaced relationship with an electrolyte disposed therebetween. A first electrode 222 is made from a first material, e.g., copper (Cu). A second electrode 224 is made from a second material, e.g., aluminum (Al). A polypropylene separator 226 separates the two electrodes. The separator 226 physically separates and prevents the electrodes from touching each other, thereby preventing electron current flow between the electrodes, but has pores therein that allows ions to pass therethrough, allowing ionic current flow between the electrodes. A suitable electrolytic paste 228 surrounds the electrode 222. Another suitable electrolytic paste 230 surrounds the electrode 224. Suitable materials from which such electrolytic pastes may be made are described in the literature. Typically, the thickness of the electrode pair, X, including separator and electrolytic paste, is on the order to 0.010 or 0.024 inches, where the Cu and Al electrodes are each about 0.001 inches thick, the separator 226 is about 0.001 inches thick or less, and the electrolytic paste on each side of the electrode is about 0.002 to 0.008 inches thick. The combination of the two electrodes 222 and 224, with separators 226, and electrolytic pastes 228 and 230 forms an electrode layer 232. A battery is formed by efficiently placing the electrode layer 232 in the available battery volume, and attaching suitable current collectors (conductors) to the positive electrode 222 and negative electrode 224 so that electrical contact may be made therewith.

The various figures shown in FIGS. 8A–8F depict various configurations that may be used to form the cylindrical shaped battery 104 needed by the present invention. Each of the individual figures shows a side sectional side view of the battery container below a cross-sectional view (as viewed, e.g., from the top) of the container.

In FIG. 8A, a length of the electrode layer 222 and 224 is rolled in spiral fashion and inserted longitudinally into a cylindrical-shaped container or case 234. Conductive wires or tabs 236 and 238 are attached to the electrodes 222 and 224 respectively and serve as the battery terminals.

In FIG. 8B, a parallel-connected interleaved stack of circular-shaped positive electrodes 222 and negative electrodes 224 are laid into a conductive container 234. Separator layers (not shown) are laid in-between the electrodes as required. The positive electrodes 222 are each connected to a bus that contacts the container 234. The negative electrodes 224 are each connected to a bus that contact a conductive lid 239 of the container 234. Alternatively, the negative electrodes 224 can be connected to the bus that contacts the container and the negative electrodes 224 can be connected to the bus that contacts the lid 239. Notches or cutouts 240 may be placed in each electrode to make a via for the buses that connect the electrodes to the container 234 or lid 239. An insulating ring 241 assures that the lid 239 does not short or touch the case 234. The container 234 and lid 239 thus function as the battery terminals.

FIG. 8C illustrates a series-connected interleaved stack. Except for the series connection, the arrangement shown in FIG. 8C is the same as that shown in FIG. 8B.

FIG. 8D shows a parallel-connected interleaved vertical stack of rectangular electrode strips, of varying width. The negative electrodes 224 are each connected to the lid 239. The positive electrodes 222 are each connected to the container 234. The container 234 and the lid 239 thus serve as the battery terminals.

FIG. 8E shows a parallel-connected concentric electrode configuration where the electrodes 222 and 224 comprise concentric tubes of different diameters that fit inside of each other.

FIG. 8F shows a wire electrode embodiment where the electrodes 222 and 224 are realized from a length of wire (approximately $L_B$) made from the appropriate material, e.g., Cu or Al, are positioned in an array such that the negative electrodes 224 are adjacent positive electrodes 222. Separator sleeves 226' are placed over the electrode wires, e.g., the negative electrode wires. The appropriate electrolytic paste fills the voids around each of the respective electrodes. As required, the separator 226' keeps the appropriate electrolytic paste around the appropriate electrode, and prevents the other electrolytic paste from coming near such area. The negative wires 224 are attached to the bottom of the container 234, and the positive wire electrodes 222 are attached to the lid 239.

Figure 8G:
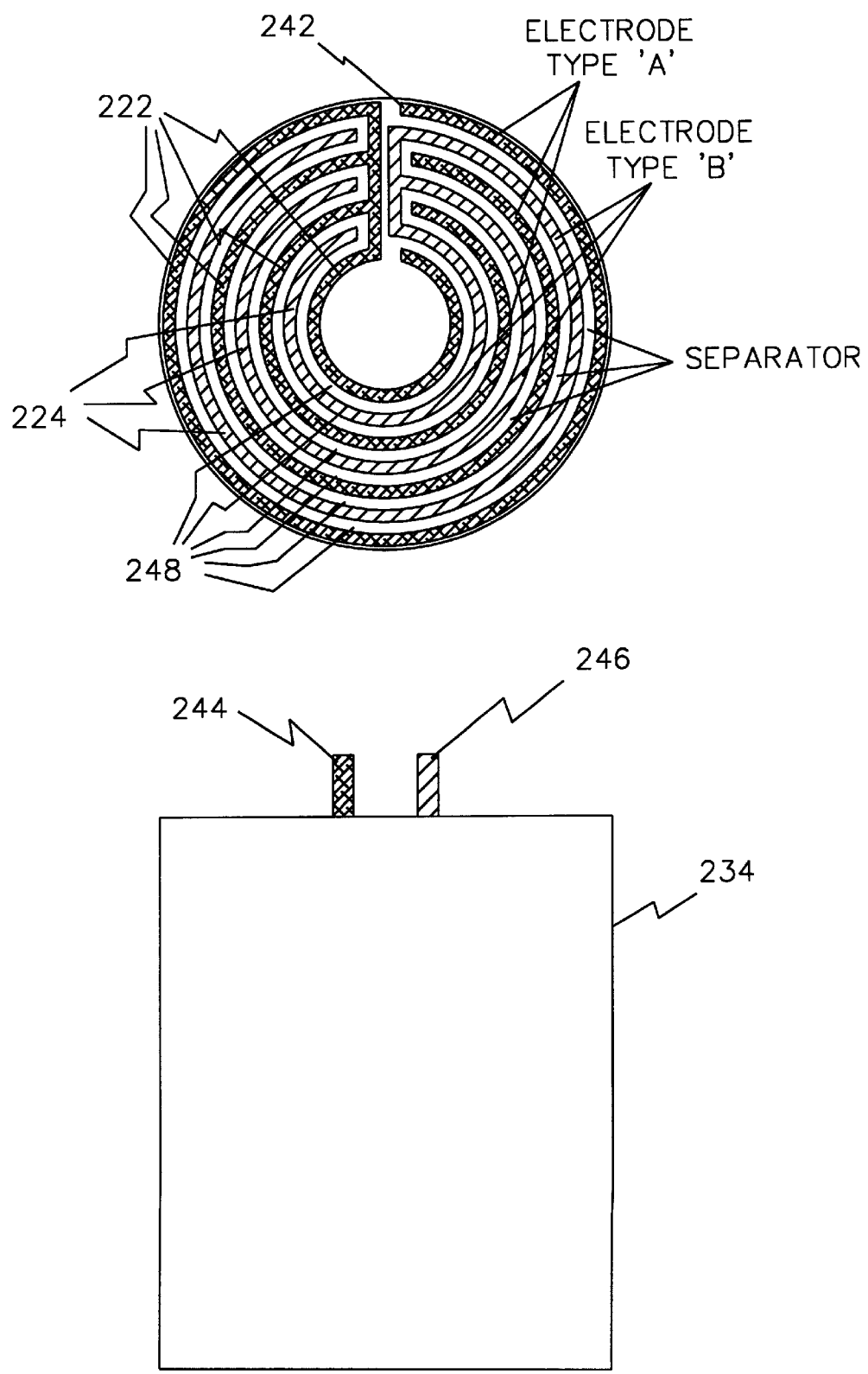

FIG. 8G shows a parallel-connected cylindrical electrode embodiment, similar to FIG. 8E, but wherein each cylindrical electrode includes a gap or slit 242; with the cylindrical electrodes 222 and 224 on each side of the gap 242 forming a common connection point for tabs 244 and 246 which serve as the electrical terminals for the battery. The electrodes 222 and 224 are separated by a suitable separator 248. The gap 242 minimizes the flow of eddy currents in the electrodes. For the embodiment shown in FIG. 8G, there are four concentric cylindrical electrodes 222, the outer one (largest diameter) of which may function as the battery case 234, and three concentric electrodes 224 interleaved between the electrodes 222, with six concentric cylindrical separator layers 248 separating each electrode 222 or 224 from the adjacent electrodes.

It is generally preferable to minimize the flow of eddy currents in the battery which could result in heat or otherwise shunting out a portion of the magnetic signal having a modulated command signal portion. As such, by not forming a battery with plates which form closed conductive loops, e.g., the configurations shown in FIG. 8A–8D and 8F, the eddy currents are minimized. However, circumstances can be envisioned where heating is desired in which case the embodiment of FIG. 8E may be desired.

Figure 9A:
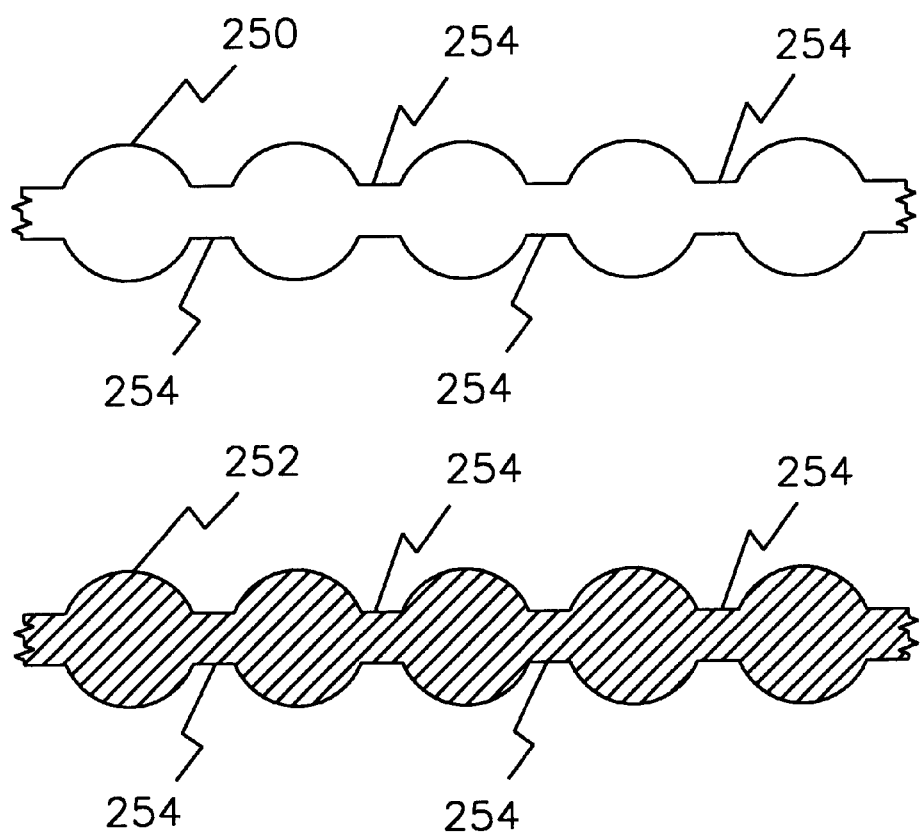
FIGS. 9A and 9B depict one manner in which the basic electrode pair may be stamped, folded and interleaved for use within a series-electrode battery configuration of the type shown in FIG. 8C.
Figure 9B:
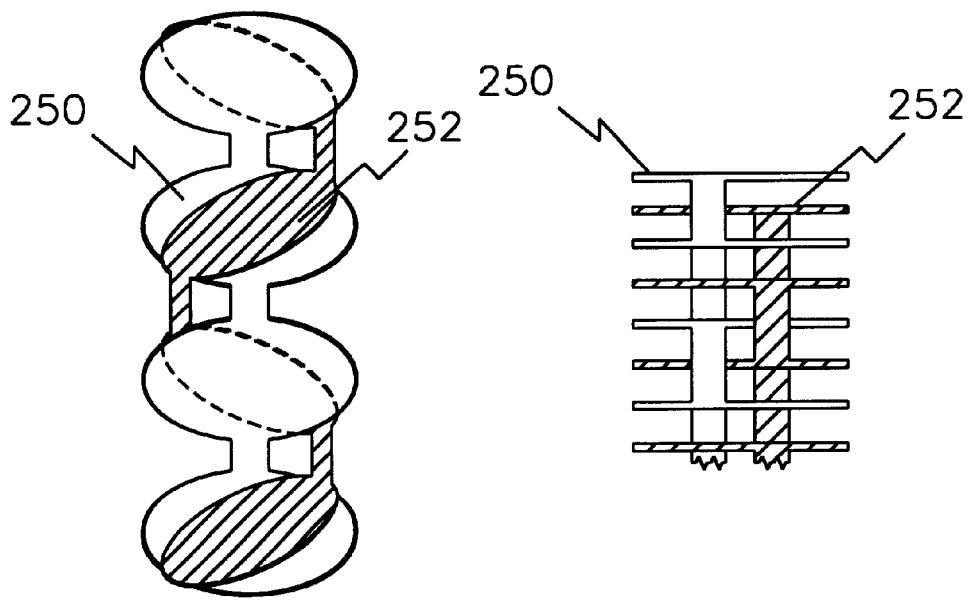

Turning next to FIG. 9A, one manner in which inexpensive electrodes may be formed for a series-connected electrode stack, such as that depicted in FIG. 8C, is illustrated. One set of electrodes 250 may be stamped and cut, e.g., from a 0.002 inch thick sheet, in a suitable pattern, such as that shown. A complementary set of electrodes 252 may likewise be stamped and cut as shown. Each set of electrodes includes the basic circular shaped electrode connected by a suitable tab 254. The tabs 254 are offset from one electrode to the next. The electrode sets are then folded and interleaved, so that the offset tabs 254 do not interfere with each other, as depicted in FIG. 9B. Each of the electrode sets 250, 252 is then inserted into the container 234, with a separator sleeve being inserted over one of the electrode sets, with an appropriate electrical connection being made between each electrode set and corresponding battery terminals.

While the invention herein disclosed has been described by means of specific embodiments and applications thereof, numerous modifications and variations could be made thereto by those skilled in the art without departing from the scope of the invention set forth in the claims. For example, while primarily magnetic and ultrasonic means of communication have been discussed, other communication means are possible. In an alternative embodiment, implantable devices 100 can communicate via conduction, i.e., modulated sub-stimulation-threshold current pulses (pulses which do not stimulate the muscles or nerves) emitted through the electrodes, infrared, or when an implanted device is implanted just under the skin, translucent optical means can be used. Additionally, other means can be used to charge the battery within the implanted device including optical (e.g., solar cells) and mechanical devices or, alternatively, a nuclear energy implementation can be used to form a suitable primary battery.

We claim:

1. A system configured for stimulating tissue internal to a patient's body, said system comprising:
   a sealed elongate housing configured for implantation in said patient's body, said housing having an axial dimension of less than 60 mm and a lateral dimension of less than 6 mm;

power consuming circuitry carried by said housing including at least one electrode extending externally of said housing, said power consuming circuitry including a capacitor and pulse control circuitry for controlling (1) the charging of said capacitor and (2) the discharging of said capacitor to produce a current pulse through said electrode;

a battery disposed in said housing electrically connected to said power consuming circuitry for powering said pulse control circuitry and charging said capacitor, said battery having a capacity of at least one microwatt-hour;

an internal coil and a charging circuit disposed in said housing for supplying a charging current to said battery;

an external coil adapted to be mounted outside of said patient's body; and means for energizing said external coil to generate an alternating magnetic field for supplying energy to said charging circuit via said internal coil.

2. The system of claim 1 wherein said battery includes first and second conductive electrodes mounted in spaced opposed relationship;

an electrolyte disposed between said first and second electrodes; and wherein said first and second electrodes are configured to minimize eddy current flow in said first and second electrodes.

3. The system of claim 2 wherein at least one of said battery electrodes is configured as a plurality of electrode elements connected in series.

4. The system of claim 1 wherein said power consuming circuitry further includes;

a controller coupled to said pulse control circuitry and responsive to stored configuration data for defining the characteristics of said current pulse; and a data signal receiver responsive to a command signal for modifying said stored configuration data.

5. The system of claim 4 further including a sensor in said housing for detecting a static magnetic field; and wherein said sensor is coupled to said controller for modifying said current pulse produced in said externally extending electrode.

6. The system of claim 5 wherein said wireless communication means includes said internal coil.

7. The system of claim 4 further including a command signal generator; and wireless communication means for coupling said command signal generator to said data signal receiver.

8. The system of claim 4 wherein said data signal receiver includes a transducer responsive to a command signal defined by a modulated ultrasonic signal.

9. The system of claim 4 wherein said power consuming circuitry further includes a data signal transmitter for transmitting a data signal.

10. The system of claim 9 wherein said transmitter includes means for transmitting a data signal in the form of a modulated magnetic field.

11. The system of claim 9 wherein said transmitter includes means for transmitting a data signal in the form of a modulated ultrasonic signal.

12. The system of claim 9 wherein said controller is selectively operable to (1) produce a sequence of drive pulses through said externally extending electrode, (2) monitor an electrical signal from said externally extending electrode, and/or (3) cause said data signal transmitter to transmit a data signal related through said command signal received by said data signal receiver.

13. The system of claim 1 wherein said charging circuit is responsive to the status of the battery coupled thereto for controlling the charging current supplied to said battery.

14. The system of claim 9 wherein said power consuming circuitry further includes means for generating a data signal representative of the status of said battery.

15. The system of claim 9 further including means for causing said transmitter to transmit a data signal related to said command signal received by said data signal receiver.

16. A system for stimulating tissue within a patient's body, said system including:

a plurality of devices configured for implantation in said patient's body, each of said devices comprising:

a housing having an axial dimension less than about 60 mm and a lateral dimension less than about 6 mm;

power consuming circuitry mounted in said housing including at least one electrode extending externally of said housing, said power consuming circuitry including:

a stimulation circuit including a capacitor, and pulse control circuitry for controlling (1) the charging of said capacitor and (2) the discharging of said capacitor to produce a current pulse through said electrode;

controller circuitry including an addressable controller for controlling said pulse control circuitry a receiver for receiving externally transmitted command signals coupled to said controller;

a battery having a capacity of at least one microwatt-hour mounted in said housing for supplying power to said power consuming circuitry;

a secondary coil mounted in said housing and coupled to said battery; and a power source adapted to be located externally of said body, for generating an alternating magnetic field for coupling energy to said secondary coil to supply a charging current to said battery.

17. The system of claim 16 wherein each of said devices further includes a signal transmitter mounted within the housing for transmitting a status signal representative of the charge state of the battery therein.

18. The system of claim 17 wherein said external charger includes means for selectively addressing said controllers to cause the signal transmitter associated with the selected controller to transmit said status signal.

19. The system of claim 17 wherein said external charger is responsive to said status signals for energizing said external coil.

20. A system configured for monitoring internal body parameters, said system comprising:

a sealed elongate housing configured for implantation in said patient's body, said housing having an axial dimension of less than 60 mm and a lateral dimension of less than 6 mm;

power consuming circuitry carried by said housing including at least one electrode extending externally of said housing, said power consuming circuitry including a sensor coupled to said electrode for providing an indication representative of a sensed body parameter and a transmitter coupled to said sensor for transmitting a signal representative of said sensed body parameter;

a battery disposed in said housing for supplying power to said power consuming circuitry, said battery having a capacity of at least one microwatt-hour;

an internal coil and a charging circuit disposed in said housing for supplying a charging current to said battery;

an external coil adapted to be mounted outside of said patient's body; and means for energizing said external coil to generate an alternating magnetic field for supplying energy to said charging circuit via said internal coil.

\* \* \* \* \*